(12) United States Patent
Salter et al.

(10) Patent No.: US 11,537,973 B2
(45) Date of Patent: Dec. 27, 2022

(54) FOOD LOCKER SANITATION SYSTEM FOR AUTONOMOUS VEHICLES

(71) Applicant: Ford Global Technologies, LLC, Dearborn, MI (US)

(72) Inventors: Stuart Salter, White Lake, MI (US); Kendra White, Redford, MI (US); Kristopher Karl Brown, Dearborn, MI (US); Zeljko Deljevic, Plymouth, MI (US); Paul Kenneth Dellock, Northville, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 509 days.

(21) Appl. No.: 16/588,676

(22) Filed: Sep. 30, 2019

(65) Prior Publication Data
US 2021/0097481 A1 Apr. 1, 2021

(51) Int. Cl.
*A61L 2/10* (2006.01)
*G06Q 10/08* (2012.01)
(Continued)

(52) U.S. Cl.
CPC ............ *G06Q 10/0832* (2013.01); *A23L 3/28* (2013.01); *A61L 2/088* (2013.01); *A61L 2/10* (2013.01);
(Continued)

(58) Field of Classification Search
CPC .... B60S 1/64; A61L 2/10; A61L 2/088; A23L 3/28
See application file for complete search history.

(56) References Cited

U.S. PATENT DOCUMENTS 6,117,362 A * 9/2000 Yen ..................... C09K 11/7734
117/946
6,477,853 B1 * 11/2002 Khorram .................. A23L 3/36
62/177

(Continued)

OTHER PUBLICATIONS

Andrew J. Hawkins, "Ford's 'self-driving' vans are now delivering food in Miami", The Verge, Jun. 11, 2-18, 4 pages.

*Primary Examiner* — Wyatt A Stoffa
(74) *Attorney, Agent, or Firm* — Brandon Hicks; Eversheds Sutherland (US) LLP (57) ABSTRACT

The systems and methods disclosed herein are directed to an autonomous vehicle food locker system that may include environmentally controlled storage compartments for storing and/or transporting perishable food items to be delivered to end consumers. The storage compartments may provide ultraviolet light controls and surfaces that provide sanitized food storage areas for a delivery vehicle. Computing processor(s) may be configured for determining a sanitization procedure for sanitizing the interior portion of the food storage locker based on sensor information received from internal and external sensors, video feeds, photographs, and other information. The processor(s) may determine one or more sanitation characteristics that can indicate or inform cleanliness of the interior portion of the food storage locker, and perform automated sanitization procedures that can include activating a chemical layer disposed on the interior portion of the food storage locker. The system may also maintain a digital record documenting the delivery process.

7 Claims, 6 Drawing Sheets

(51) Int. Cl.
    *G05D 1/00*    (2006.01)
    *A23L 3/28*    (2006.01)
    *B60S 1/64*    (2006.01)
    *A61L 2/08*    (2006.01)

(52) U.S. Cl.
    CPC .............. *B60S 1/64* (2013.01); *G05D 1/0088* (2013.01); *G06Q 10/0833* (2013.01); *A61L 2202/14* (2013.01)

(56) References Cited

U.S. PATENT DOCUMENTS

| | | | |
|---|---|---|---|
| 10,046,688 B2 | 8/2018 | Salter et al. | |
| 10,849,996 B2 * | 12/2020 | Shur | H04N 7/183 |
| 11,027,319 B2 * | 6/2021 | Shatalov | A61L 2/10 |
| 2005/0242301 A1 * | 11/2005 | Pierce | A61L 2/04 |
| | | | 250/492.2 |
| 2014/0060094 A1 * | 3/2014 | Shur | F25D 27/005 |
| | | | 422/186.3 |
| 2014/0060096 A1 * | 3/2014 | Shur | A61L 2/10 |
| | | | 250/492.1 |
| 2014/0060104 A1 * | 3/2014 | Shur | F25D 17/042 |
| | | | 250/492.1 |
| 2014/0061509 A1 * | 3/2014 | Shur | A23L 3/003 |
| | | | 250/492.1 |
| 2015/0069270 A1 * | 3/2015 | Shur | F25D 17/042 |
| | | | 250/492.1 |
| 2015/0374868 A1 * | 12/2015 | Bruce | A61L 2/07 |
| | | | 422/119 |
| 2016/0217417 A1 * | 7/2016 | Ma | G06V 20/52 |
| 2017/0228742 A1 * | 8/2017 | Aljawhari | G06Q 30/0185 |
| 2018/0117195 A1 * | 5/2018 | Dobrinsky | G02B 6/0003 |
| 2018/0169286 A1 * | 6/2018 | Henniges | A61L 2/208 |
| 2018/0221521 A1 * | 8/2018 | Shur | A61L 2/10 |
| 2018/0264151 A1 * | 9/2018 | Shur | F25D 17/042 |
| 2018/0272018 A1 * | 9/2018 | Shur | F25D 17/042 |
| 2019/0019378 A1 * | 1/2019 | Greiner | G03B 17/54 |
| 2019/0034857 A1 * | 1/2019 | Ferguson | B60R 25/252 |
| 2019/0209725 A1 * | 7/2019 | Henniges | A61L 2/24 |
| 2020/0051012 A1 * | 2/2020 | Deemter | G06Q 10/0832 |
| 2020/0061223 A1 * | 2/2020 | Hallack | B60N 2/002 |
| 2020/0268921 A1 * | 8/2020 | Lepine | A61L 2/08 |
| 2020/0284416 A1 * | 9/2020 | Greiner | F21V 23/0478 |
| 2020/0289686 A1 * | 9/2020 | Janik | G01V 11/002 |
| 2022/0031887 A1 * | 2/2022 | Hopkins | D06M 16/00 |
| 2022/0031894 A1 * | 2/2022 | Deshays | A61L 2/085 |

\* cited by examiner

FIG. 1

VIEW 2-2

FOOD LOCKER SANITATION SYSTEM FOR AUTONOMOUS VEHICLES

TECHNICAL FIELD

The present disclosure relates to autonomous vehicle systems, and more particularly, to an automated container sanitation and alert system for an autonomous delivery vehicle.

BACKGROUND

Autonomous vehicles are envisioned as an opportunity to provide quick on-demand delivery for various services and products, including food. Conventional food distribution may include multiple human actors that must handle the food, load the food into delivery vehicles, and drive the food to the consumer. Autonomous vehicles, without human actors to monitor and upkeep the cleanliness of the food storage areas, may have additional challenges in maintaining a sanitary environment for food distribution. For example, as individuals retrieve their food from a storage locker of an autonomous vehicle, humans, animals, or other environmental factors may introduce unclean conditions when they come into contact with food storage areas, which may contaminate future orders delivered by that vehicle.

Using conventional human delivery personnel, consumers receiving the food delivery may have an opportunity to observe the cleanliness of the delivery vehicle and personnel, which can provide some indication as to the cleanliness of the process that brought the food to their door. When the chain of food handling is unknown, or there are no visual cues as to the sanitation of the delivery environment, the consumer may have decreased confidence that the food was well-handled, with sanitary conditions and equipment.

Food distribution using autonomous vehicles is disclosed in U.S. Pat. No. 10,046,688 (hereafter "the '688 publication"), which includes an autonomous vehicle having a light source that illuminates sales bins disposed on the vehicle that can carry food items. The '688 publication describes an autonomous food delivery vehicle having an awning and a camera that captures images and other data of the food storage areas onboard the vehicle. While the '688 publication discloses autonomous vehicles having light sources and photoluminescent structures that convert light input received from LED sources into different color light output, the '688 publication does not address concerns about sanitary conditions of the food storage areas. For example, the '688 publication does not determine whether the food storage areas are sanitized, does not provide remedial steps to provide sterilization, and does not provide communications to consumers or other personnel indicative of whether the food storage bins are clean and sanitary.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

The systems and methods disclosed herein are directed to an autonomous vehicle food locker system that may include environmentally controlled storage compartments for storing and/or transporting perishable food items to be delivered to end consumers. The food storage compartments may be equipped with ultraviolet light sanitation controls and surfaces that may provide clean and sanitized food storage areas for the autonomous vehicle's delivery payload.

Embodiments may use ultraviolet (UV) light exposure applied to a chemically treated interior surface to provide the sterilization aspects. For example, the UV light may activate a catalytic reaction in a surface coating disposed in the interior surfaces of the food storage locker that causes the food locker to break down any residual organic matter, eliminate and/or reduce bacteria, molds, funguses, viruses, etc., as well as remove odors in the food locker. The UV light may cause any fluids and/or organic contaminants to fluoresce, which provides visual proof to a consumer that the food locker is clean and sanitary.

In one example embodiment, a chemical layer that includes a long persistence phosphor surface coating may be disposed on a plurality of interior surfaces of the food storage locker such that they provide photoluminescent output after exposure to a UV photonic input stimulus. The long-persistence phosphor surface coating may provide a visual indication for consumers receiving the food delivery that the food storage locker is sanitary. For example, white pigments in the chemical layer can provide, at least in part, an overall impression of the sanitation conditions. When energized, the chemical layer may generate blue light that illuminates the interior of the food storage locker, and may provide a visual cue to the consumer that the storage area has been sanitized and maintained in a proper food-ready condition. The blue illumination may render organic containments visible by fluorescence from the phosphor luminescence, which may be more readily visible when seen against the white-pigmented interior surface.

In other aspects, the long-persistence phosphor coating in the chemical layer may biologically sanitize the interior of the food storage bin when used with photonic stimulus such as, for example, UV light. For example, the surface coating may include a titanium dioxide additive having pigmentation and antibacterial properties when lit by the UV light source(s) for a predetermined threshold of time, and at a predetermined range of photonic wavelength. For example, when illuminated with UV light having wavelengths ranging from 260 to 380 nm, the photonic stimulus may charge long-persistence phosphor in the coating such that bioactivity associated with bacteria outgrowth, fungal spores, viruses, and other contaminants proximate to the interior surfaces of the food locker may be substantially reduced and/or eliminated.

Example embodiments may include one or more UV Light Emitting Diode (LED) devices and white (full-spectrum) LED devices disposed on an interior surface of the storage locker. In other aspects, embodiments may include one or more audio visual sensors disposed in communication with one or more processor(s) and positioned on one or more inside and/or outside surfaces of the storage locker. The sensor(s) may provide audio, video, proximity, thermal, and/or other information indicative of environmental aspects of the food storage areas. One or more access control mechanisms may be disposed on an exterior surface of the storage bin, providing security-enabled access to interior spaces of the bin with a code, facial recognition, key fob, radio frequency identification (RFID) device, and/or the like. In some aspects, the access control, LED controller(s), and communications components such as a display may be integrated into a unified control unit disposed on a door of the storage locker such that a single Printed Circuit Board (PCB) provides access control and functional aspects.

In some aspects, the processor(s) may retrieve sensor information, including image data, time data, temperature information, etc., at periodic intervals to determine and document a state of cleanliness associated with the interior of the food storage lockers, to identify and to document environmental conditions associated with food safety during transportation. The processor(s) may also retrieve image information and/or authentication information to identify individuals associated with various stages of food preparation, loading, and transportation using the food storage bins and the delivery vehicle.

For quality assurance, time stamped pictures (e.g., using the white LED) output devices disposed on the interior of the food storage locker are automatically taken at every stage of the food preparation, loading, transportation and removal process. The system may use pattern-matching techniques to automatically identify conditions indicative of clean and sanitary conditions for food storage lockers by evaluating differences in compared images, and matching the differences (potential contamination or soil) with patterns saved in a database. These images may also associate a human actor responsible for loading/unloading the food locker or otherwise affecting the food stored in the locker at the time the image was taken (this may include a consumer opening/replacing a bin located in the food locker).

According to embodiments, the photonic stimulus provided to interior surfaces of the storage locker, for a predetermined threshold of time, may substantially reduce and/or eliminate adenosine triphosphate (ATP) associated with biological outgrowth on interior surfaces of the food storage locker. The ATP may be reduced to a sterility measurement having a value within a predetermined range of biological indication, as measured by acid production or other known methods for sterilization quantification. Example embodiments described herein may also provide other benefits over conventional methods for autonomous food distribution including automated sterilization of the food delivery mechanism, documentation of the cleanliness of the food delivery mechanism, and full documentation of environmental considerations associated with the payload being delivered throughout the full chain of custody of the payload.

These and other advantages of the present disclosure are provided in greater detail herein.

ILLUSTRATIVE EMBODIMENTS

The disclosure will be described more fully hereinafter with reference to the accompanying drawings, in which exemplary embodiments of the disclosure are shown, and not intended to be limiting.

Figure 1:
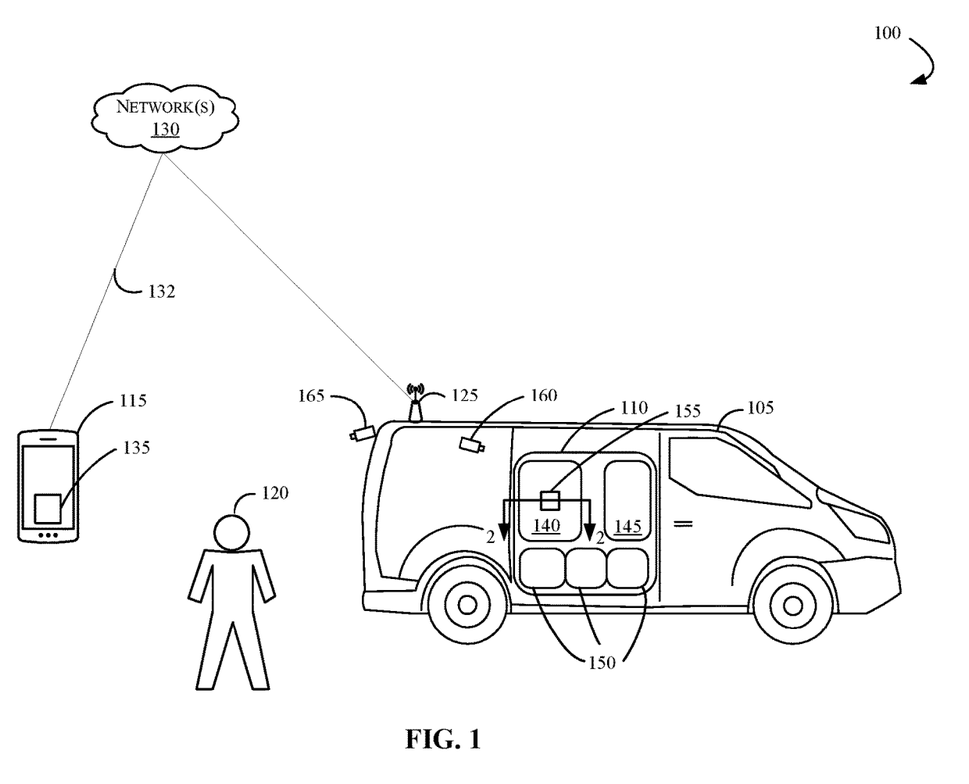
FIG. 1 depicts an example computing environment in which techniques and structures for providing the systems and methods disclosed herein may be implemented.

FIG. 1 depicts an example computing environment 100 that can include one or more vehicle(s) 105 configured with a food storage locker system 110. The food storage locker system 110 is a computing system associated with a printed circuit board (PCB) assembly 155 that may be used at least in part, to determine sanitization conditions associated with the food storage lockers onboard the vehicle 105. The PCB assembly 155 may communicate information to other devices such as, for example, a mobile device 115, associated with a consumer 120. In some aspects, the vehicle 105 may include one or more communications devices, such as a transceiver 125 disposed in communication with the mobile device 115 and/or other computing systems (not shown in FIG. 1) via one or more network(s) 130. The mobile device 115 may include one or more application(s) 135 disposed in communication with the food storage locker system 110. The application(s) 135 may provide the consumer 120 with information associated with the food delivery performed by/with the vehicle 105, including, for example, by providing one or more indication(s) of the cleanliness of the food storage locker system 110. The indications can include, for example, one or more video feeds, photos, sensor data, time information, date information, contact information, and other information.

Although illustrated as a delivery van, the vehicle 105 may take the form of another passenger or commercial automobile such as, for example, a car, a truck, a sport utility vehicle, a crossover vehicle, a taxi, a bus, etc. Further, although preferred embodiments described herein may be directed to an autonomous vehicle, it is appreciated that the vehicle 105 may be a manually driven vehicle, and/or be configured to operate in a fully autonomous (e.g., driverless) mode or partially autonomous mode. In other aspects, the vehicle 105 may include another configuration suitable to transport food using the food storage locker system 110, as described herein in one or more embodiments.

In some aspects, the mobile device 115 may communicate with the vehicle 105 through one or more channel(s) 132, which may be encrypted or unencrypted, and established between the mobile device 115 and the food storage locker system 110. The mobile device 115 may communicate with the food storage locker system 110 using the transceiver 125 associated with the food storage locker system 110 on the vehicle 105. The transceiver 125 may communicate with the mobile device 115 using a wireless communication network such as, for example, the network(s) 130.

The network(s) 130 illustrate an example of a communication infrastructure in which the connected devices may communicate. The network(s) 130 may be the Internet, a private network, public network or other configuration that operates using any one or more known communication protocols such as, for example, transmission control protocol/Internet protocol (TCP/IP), Bluetooth®, Wi-Fi, and cellular technologies such as Time Division Multiple Access (TDMA), Code Division Multiple Access (CDMA), High Speed Packet Access (HSPDA), Long-Term Evolution (LTE), Global System for Mobile Communications (GSM), and Fifth Generation (5G), to name a few examples.

In some aspects, the food storage locker system 110 may include a plurality of self-sanitizing compartments for storing and transporting food items, and other items associated with food delivery, such as cutlery, condiments, paperware, etc. The food storage locker system 110 (hereafter "system 110") may include one or more compartments such as a food storage locker 140 and a food storage locker 145, which may be self-sanitizing and self-monitoring, according to example embodiments described herein. In other aspects, the system 110 may include one or more storage bins 150, which may be non-automated storage bins, receptacles, compartments, etc. The storage bins 150 may be substantially similar to and/or identical to the food storage lockers 140 and 145, but different in size, shape, and/or payload capability. For example, it may be advantageous to include storage bins 150 having self-sanitization and monitoring capability, yet sized appropriately such that cutlery or other small food items may be stored therein. In one embodiment, the one or more of the storage bins 150 may include a printed circuit board controllable to perform aspects of the present disclosure similar to the food storage locker 140 and/or 145.

Figure 2:
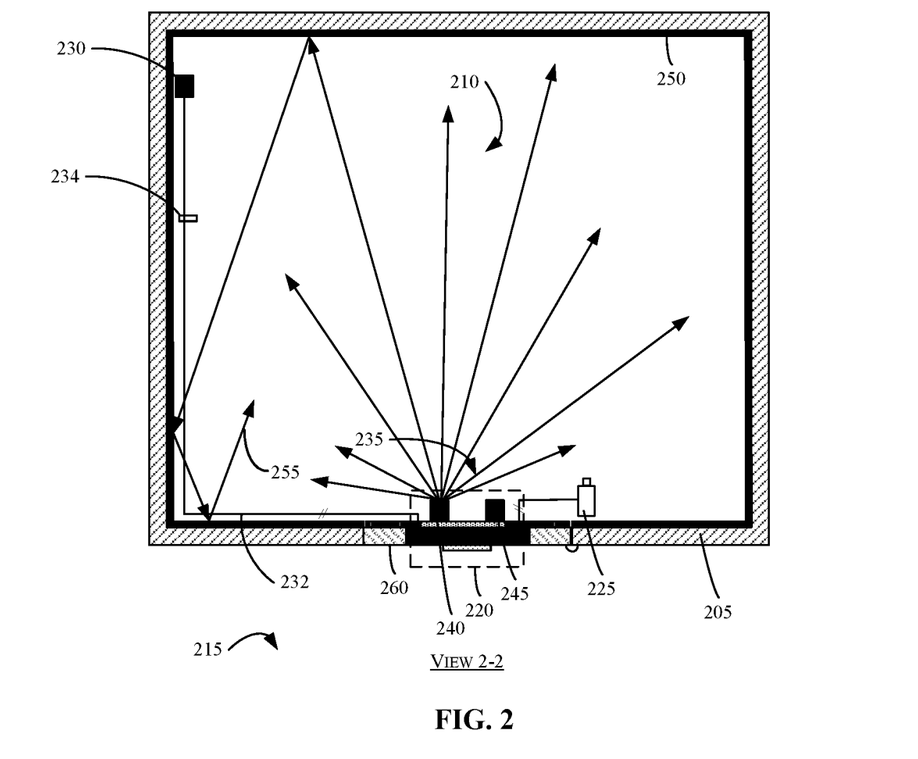
FIG. 2 depicts an example food storage locker having a printed circuit board assembly with which methods disclosed herein may be implemented.

The compartments having self-sanitizing systems may include one or more integrated printed circuit board (PCB) assemblies, such as the PCB assembly 155 shown in FIG. 1 as being disposed on a door 260 (as shown in FIG. 2) of the food storage locker 140. The PCB assembly 155 may include connectivity with one or more sensors inside the food storage locker 140, such as, for example, one or more exterior cameras 160 and 165, and environmental sensors such as, for example, a thermometer, hydrometer, humidistat, and/or other sensing or other equipment such as, for example an input device, an output device, access control components such as keypads, biometric input devices, etc. An example PCB assembly 400 is depicted hereafter with respect to FIG. 4. A set of section arrows view 2-2 demarks a partial section view of the food storage locker system 110 which is discussed in greater detail with respect to FIG. 2.

FIG. 2 depicts an example section view 2-2 of the food storage locker 140, according to an embodiment of the present disclosure. The food storage locker 140 may include an insulated or non-insulated enclosure body 205 having an interior portion 210 in which food items (not shown in FIG. 2) can be stored and maintained during placement, transportation and delivery according to environmental conditions suitable for such perishable food storage. For example, in one aspect, the food storage locker 140 may be a refrigerated locker or a heated locker, etc. In another embodiment, the food storage locker 140 may be a cold-storage locker that maintains temperatures below freezing. Other configurations are possible, and contemplated.

The food storage locker 140 may include the PCB assembly 155 (FIG. 1) that may provide and/or prevent access to the interior portion 210 of the food storage locker 140. Although depicted in FIG. 2 as being integrated with a door 260, it should be appreciated that the PCB assembly 155 may be configured on any surface of the food storage locker 140, and should not be considered as limited to the illustrated embodiment.

In some aspects, the PCB assembly 220 may be configured and/or programmed to receive sensor information from one or more sensors disposed in communication with the PCB assembly 220. The PCB assembly 220 may be substantially similar to and/or identical to the PCB assembly 155 depicted in FIG. 1. In other aspects, the PCB assembly 220 may further receive sensor information 234 from an interior camera 225, via a sensor bus 232, where the sensor information 234 can include video feed data indicative of visible contaminants, spillage, etc., in the interior portion 210 of the food storage locker 140. The sensor information 234 may also include data from the one or more exterior cameras 160 and/or 165 that can show video feed and/or other identity information associated with individuals in contact with food items stored in the food storage locker 140. In one example, the exterior camera 165 and/or the exterior camera 160 may obtain a video feed of an individual (not shown in FIG. 1) placing food items in the food storage locker 140, and/or individuals receiving delivery of the food items, such as the consumer 120. The PCB assembly 220 may receive the video feed, document and/or identify individual(s) in contact with the food storage locker 140, and provide the documentation to the consumer 120 via the application 135. Accordingly, the food storage locker 140 may fully document any events that may affect sanitary conditions associated with delivery of the food using the food storage locker 140. Additionally, the PCB assembly 220 may determine, based at least in part on the sensor information, an identity associated with a food provider, a consumer, or another individual, who may have accessed the food storage locker 140 and interacted with the interior portion of the food storage locker 140.

The PCB assembly 220 may further include and/or may be disposed in communication with a sensor array 230 that can provide information indicative of environmental conditions of the interior portion 210. For example, the PCB assembly 220 may receive sensor information 234 from sensor array 230, via a sensor bus 232. The sensor information 234 may be indicative of sanitation characteristics associated with the interior portion 210 of the food storage locker 140. For example, the PCB assembly 220 may receive the sensor information indicative of one or more sanitation characteristics of the interior portion 210 of the food storage locker 140, such as, temperature, humidity, light content, biological activity, etc. In other aspects, the PCB assembly 220 may also receive temperature data associated with an exterior portion 215 of the food storage locker 140, and time information associated with operation of a door latch (not shown in FIG. 2) that provides access to the interior portion 210 of the food storage locker 140. For example, the sensor array 230 may include one or more proximity sensors (not shown in FIG. 2) that may provide signals usable to determine motion, determine an open condition of the door 260, determine a closed condition of the door 260, etc.

The PCB assembly 220 may further include and/or be disposed in communication with a photonic output array 235. The photonic output array 235 may include one or more of an UV photonic output device 240 and a full-spectrum photonic output device 245. A chemical layer 250 may be disposed on any or all interior surfaces of the food storage locker 140 such that the chemical layer 250 may receive light energy from the photonic output array 235 through direct and/or reflected 255 UV photonic output. The photonic output array 235 may be disposed in communication with the PCB assembly 220 and include one or more light emitting diodes (LEDs) configured to produce photonic output that eliminates and/or substantially reduces contaminants and pathogens in the interior portion 210. The photonic output array 235 may sanitize the interior portion 210 of the food storage locker 140 in two distinct ways: first, the UV light content may directly eliminate the contaminants. In some aspects, the photonic output array 235 may produce photonic stimulus for a predetermined period of time (e.g., 1 minute, 5 minutes, etc.) sufficient to neutralize and/or eliminate the contaminants and pathogens using direct exposure to UV light.

The photonic output array 235 may also sanitize the interior portion 210 in another way, by the interaction of UV light with the chemical layer 250. For example, in some embodiments, the photonic stimulus 235 may include output of UV light having a predetermined wavelength, where the light stimulus has various effects on the chemical layer 250. In one example embodiment, the chemical layer 250 may include a titanium dioxide chemical layer, which may eliminate and/or substantially reduce bacteria, viruses, and other biological agents when in contact with the energized phosphor content of the chemical layer 250.

In other aspects, the chemical layer 250 may include a long-persistence phosphor portion that receives the UV photonic output associated with the photonic output array 235, and chemically stores the photonic output such that the light energy may be released in the form of a blue light that can illuminate the interior of the food storage locker 140. Accordingly, when the UV photonic output is ceased, and the food storage locker is opened, the interior portion 210 of the food storage locker 140 may glow blue, which may provide supplemental light to view food items, and also make any contaminants obvious to viewers (e.g., the consumer 120) opening the food storage locker 140. This feature may also provide a visual indication that the interior portion 210 is clean and sanitary.

Figure 5:
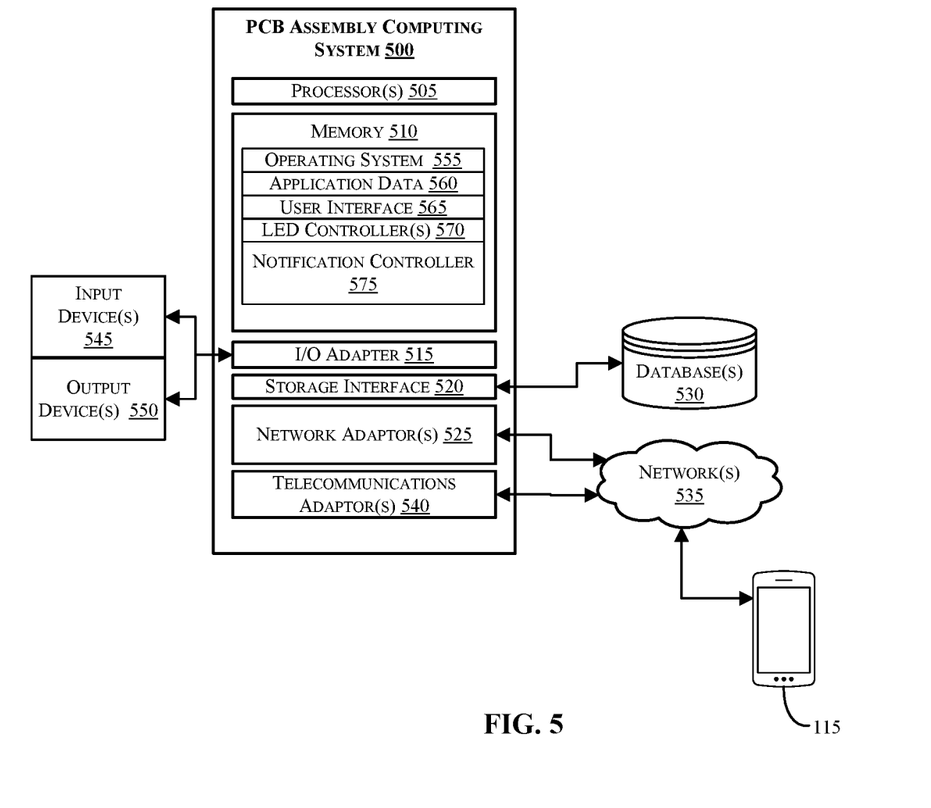
FIG. 5 depicts a computing architecture with which techniques and methods disclosed herein may be implemented.

In other embodiments, the full-spectrum photonic output device 245 may provide additional light output for an interior camera 265 to capture any action by individuals opening the door 260, and to provide periodic photographic evidence of the state of the interior of the food storage bin at predetermined time intervals (e.g., every 10 minutes, 5 minutes, 1 minute, etc.). This feature may provide a full chain of evidence indicative of how food being delivered to a consumer was handled from the time it was placed in the food storage locker 140, through navigation and delivery of the payload to the consumer 120. In one aspect, the full-spectrum photonic output device 245 may generate output (which may be full-spectrum and/or other light content) when triggered by an opening of the door 260, by actuation of a door latch (not shown FIG. 2), or via another trigger. In other aspects, the full-spectrum photonic output device 245 may light the interior portion 210 such that video and/or camera data may be compared to determine one or more sanitation characteristics of the interior portion 210 of the food storage locker 140. For example, a system processor (e.g., the processor(s) 505 described in greater detail with respect to FIG. 5) may receive the sensor information 234, where the sensor information includes a first image of the interior portion 210, and match, based at least in part on the sensor information 234, a sanitization characteristic of the one or more sanitation characteristics in a characteristics database (e.g., one or more database(s) 530 as depicted in FIG. 5 hereafter). The sanitation characteristics database may include data for pattern matching techniques that match particular sources of contamination (e.g., a particular type of spill or contamination that may or may not require full re-deployment of another food storage locker) to remediation steps (e.g., light sterilization for a first type of contamination, a longer light sterilization for another type of contamination, a message generation for yet another type of contamination, etc.). In other aspects, the pattern matching techniques may also provide instructions for controlling the photonic output devices to produce particular photonic output having specific wavelength content, specific time over which the light is output, etc. Accordingly, the processor(s) 505 may determine, based at least in part on the sanitization characteristic, the sanitization procedure for the interior portion 210 of the food storage locker 140.

In other aspects, the remediation steps may also include generation and transmission of a message indicating a need to dispatch other modes of food transportation due to contamination that renders the food storage locker 140 unusable until cleaning.

In one embodiment, the sources of contamination may include various characteristics, such as, for example, a fingerprint characteristic, a grease or oil characteristic, a water or other non-oil characteristic, a food solids characteristic, etc. Other characteristics are possible, and contemplated.

Figure 3:
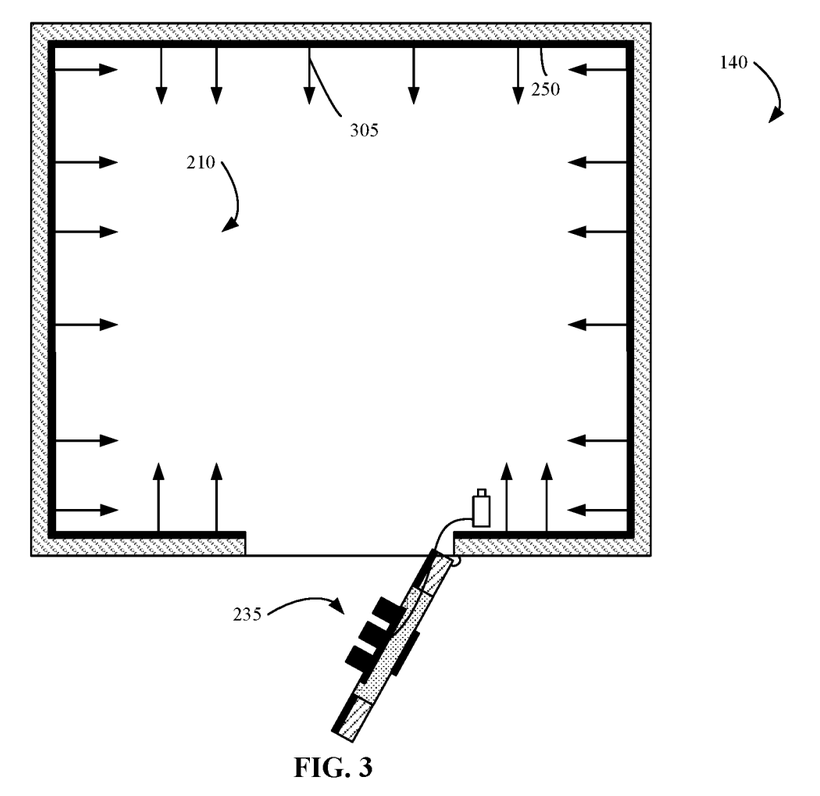
FIG. 3 depicts the example food storage locker of FIG. 2 after activating a chemical layer disposed on interior surfaces of the storage locker according to an embodiment of the present disclosure.

FIG. 3 depicts the food storage locker 140 after performing the sanitization procedure, where the sanitization procedure includes activating the chemical layer 250 disposed on the interior portion 210 of the food storage locker 140. For example, activating the chemical layer 250, in one aspect, may include generating UV light with the photonic output array 235 disposed on the interior portion 210 of the food storage locker 140, and energizing a long-persistence phosphor portion of the chemical layer 250 via UV photonic output 255 (as shown in FIG. 2) associated with the photonic output array 235. Once energized, the chemical layer 250, and more particularly, the long-persistence phosphor portion of the chemical layer 250 may generate bioluminescence 305 for a period of time after activation.

Figure 4:
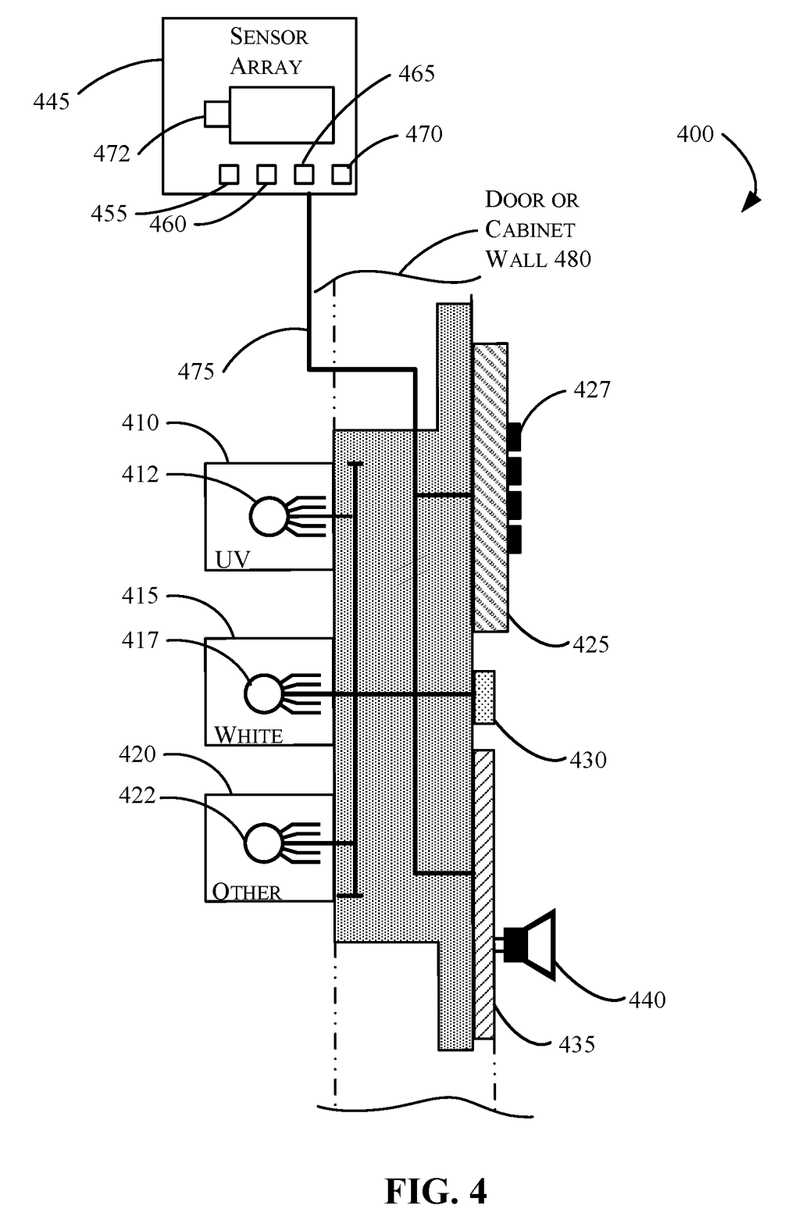
FIG. 4 is a section view of a printed circuit board assembly according to an embodiment of the present disclosure.

FIG. 4 depicts an example PCB assembly 400 in accordance with an embodiment of the present disclosure. The PCB assembly 400 may be disposed in a door or cabinet wall 480 of a food storage locker system (e.g., the system 110 depicted with respect to FIG. 1). In one embodiment, the PCB assembly 400 may include a sensor array 405 that can include one or more of an UV photonic output device 410 having one or more LEDs 412, a full-spectrum photonic output device 415 having one or more LEDs 417, and one or more other photonic output devices 420 that may include one or more other photonic output components 422.

The PCB assembly 400 may further include an access control input device 425, a keypad 427, and an audio/video input device 430. The PCB assembly 400 may be disposed in communication a sensor array 445 having any number and type of sensory devices including, for example, one or more humidity sensor(s) 455, one or more photometric sensor(s) 460 and other sensor(s) 465. The sensor array 445 may further include one or more proximity sensors 470, that may determine whether there are food items in the food storage locker. The PCB assembly 400 may include an integrated camera 472, and/or may be disposed in communication with external camera(s) via a sensor bus 475.

It should be appreciated that the PCB assembly 400 may be a unified assembly that can provide sensory, processing, communication, and actuation aspects as described herein, where a single unit may be installed as one piece into a door or cabinet wall 480 of a food storage locker (e.g., the food storage locker 140 depicted in FIG. 1). The PCB assembly 400 is considered unified in that it may be installed as a single unit connectable to the sensor array 445 and a system power source (not shown). A unified PCB assembly such as the example PCB assembly 400 can provide convenience and efficiency when installing, maintaining, and replacing control mechanisms in food storage locker systems such as the system 100 depicted in FIG. 1.

FIG. 5 illustrates a block diagram of an exemplary PCB assembly computing computer system 500 (hereafter "computing system 500") for use in practicing the embodiments described herein. The environment and system described herein can be implemented in hardware, software (e.g., firmware), or a combination thereof. The computing system 500 may be part of the PCB assembly 155, the PCB assembly 400, such that components of FIG. 5 are functionally integrated as part of the example PCB assemblies described herein.

As shown in FIG. 5, the computing system 500 may include the one or more processor(s) 505, memory 510 communicatively coupled to the one or more processor(s) 505, and an input/output (I/O) adaptor 515 that can communicatively connect with external devices. The computing system 500 may operatively connect to and communicate information (e.g., the sensor information 234 as shown in FIG. 2) with one or more internal and/or external memory devices such as, for example, one or more databases 530 via a storage interface 520. The computing system 500 may include one or more network adaptor(s) 525 enabled to communicatively connect the computing system 500 with one or more network(s) 535. The network(s) 535 may be the network(s) 130 shown in FIG. 1, and/or may include other network infrastructure(s). In some example embodiments, the network(s) 535 may be or include a telecommunications network infrastructure. In such embodiments, the computing system 500 can further include one or more telecommunications adaptor(s) 540. The computing system 500 may further include and/or connect with one or more input devices 545 and/or one or more output devices 550 through the I/O adaptor 515.

The one or more processor(s) 505 are collectively a hardware device for executing program instructions (aka software), stored in a computer-readable memory (e.g., the memory 510). The one or more processor(s) 505 can be a custom made or commercially-available processor, a central processing unit (CPU), a plurality of CPUs, an auxiliary processor among several other processors associated with the computing system 500, a semiconductor-based microprocessor (in the form of a microchip or chip set), or generally any device for executing instructions.

The one or more processor(s) 505 may be disposed in communication with one or more memory devices (e.g., the memory 510 and/or one or more databases 530, etc.) via a storage interface 508. The storage interface 508 can also connect to one or more memory devices including, without limitation, one or more databases 530, and/or one or more other memory drives (not shown) including, for example, a removable disc drive, a vehicle computing system memory, cloud storage, etc., employing connection protocols such as serial advanced technology attachment (SATA), integrated drive electronics (IDE), universal serial bus (USB), fiber channel, small computer systems interface (SCSI), etc.

The memory 510 can include any one or a combination of volatile memory elements (e.g., dynamic random access memory (DRAM), synchronous dynamic random access memory (SDRAM), etc.) and can include any one or more nonvolatile memory elements (e.g., erasable programmable read-only memory (EPROM), flash memory, electronically erasable programmable read-only memory (EEPROM), programmable read-only memory (PROM), etc.

The instructions in the memory 510 can include one or more separate programs, each of which can include an ordered listing of computer-executable instructions for implementing logical functions. In the example of FIG. 5, the instructions in the memory 510 can include an operating system 555. The operating system 555 can control the execution of other computer programs such as, for example, a sanitation procedure engine (not shown in FIG. 5) configured to perform analytical steps described herein such as pattern matching a sanitization characteristic observed from one or more video feeds associated with the system 110 and/or based on the sensor information 234. The computer programs controlled, at least in part, by the operating system 555 may perform other steps such as matching the one or more sanitation characteristics in a characteristics database (that may be part of the database(s) 530), and determine, based at least in part on the sanitization characteristic, the sanitization procedure for the interior portion 210 of the food storage locker (140, for example). The sanitation procedure engine may further provide scheduling, input-output control, file and data management, memory management, and communication control and related services. For example, the instructions in the memory 510 can cause the processor(s) 505 to activate a photonic output array disposed on an interior surface of the food storage locker 140, and energize a long-persistence phosphor portion of the chemical layer 250 using an UV photonic output device 240 associated with the photonic output array 235.

The program instructions stored in the memory 510 can further include application data 560, and instructions for controlling and/or interacting with the computer through a user interface 565. The user interface 565 may be substantially similar to and/or identical to the touchscreen output device 425 and/or the keypad 427 (described with respect to FIG. 4).

One or more LED controller(s) 570 may be programmed and/or configured to control the photonic output devices such as, for example, the UV photonic output device 410 (as shown in FIG. 4), the full-spectrum photonic output device 415 (as shown in FIG. 4), etc.

A notification controller 575 may be configured to generate one or more messages to consumers and/or other connected devices that indicate tasks to be performed that maintain cleanliness for system 100, that indicate delivery-related messages, and other messages.

The I/O adaptor 515 can connect a plurality of input devices 545 to the PCB assembly computing system 500. The input devices can include, for example, a keyboard, a mouse, a microphone, a sensor, etc. The output device 550 can include, for example, a display, a speaker, a touchscreen, etc.

The I/O adaptor 515 can further include a display adaptor coupled to one or more displays. The I/O adaptor 515 can be configured to operatively connect one or more input devices 545 to the computing system 500. For example, the I/O adaptor 515 can connect a keyboard and mouse, a touchscreen, a speaker, a haptic output device, or other output device such as, for example, the audio output device 440 (shown in FIG. 4). The output devices 550 can include but are not limited to a printer, a scanner, a speaker, a video display, an LED array or other device, and/or the like. Other output devices can also be included and are contemplated, although not shown in FIG. 5. Finally, the I/O devices connectable to the I/O adaptor 515 can further include devices that communicate both inputs and outputs (not shown in FIG. 5), for instance but are not limited to, a network interface card (NIC) or modulator/demodulator (for accessing other files, devices, systems, or a network), a radio frequency (RF) or other transceiver, a telephonic interface, a bridge, a router, and the like.

According to some example embodiments, the PCB assembly computing system 500 can include a mobile communications adaptor 540. The mobile communications adaptor 540 can include a global positioning system (GPS), cellular, mobile, and/or other communications protocols for wireless communication. In one aspect, the transceiver 125 (depicted in FIG. 1) may be substantially similar and/or identical to the telecommunications adaptor(s) 540. In some embodiments, the computing system 500 can further include communications adaptor 516 for coupling to the network(s) 535.

The network(s) 535 may be the Internet, a private network, public network or other configuration that operates using any one or more known communication protocols such as, for example, transmission control protocol/Internet protocol (TCP/IP), Bluetooth®, Wi-Fi, and cellular technologies such as Time Division Multiple Access (TDMA), Code Division Multiple Access (CDMA), High Speed Packet Access (HSPDA), Long-Term Evolution (LTE), Global System for Mobile Communications (GSM), and Fifth Generation (5G), to name a few examples. In one embodiment, the network(s) 535 can include one or more IP-based network(s) for communication between the computing system 500 and any external device. The network(s) 535 may transmit and receive data between the computing system 500 and devices and/or systems external to the computing system 500. For example, the network(s) 535 can also be and/or include a packet-switched network such as a local area network, wide area network, metropolitan area network, the Internet, or other similar type of network environment.

Figure 6:
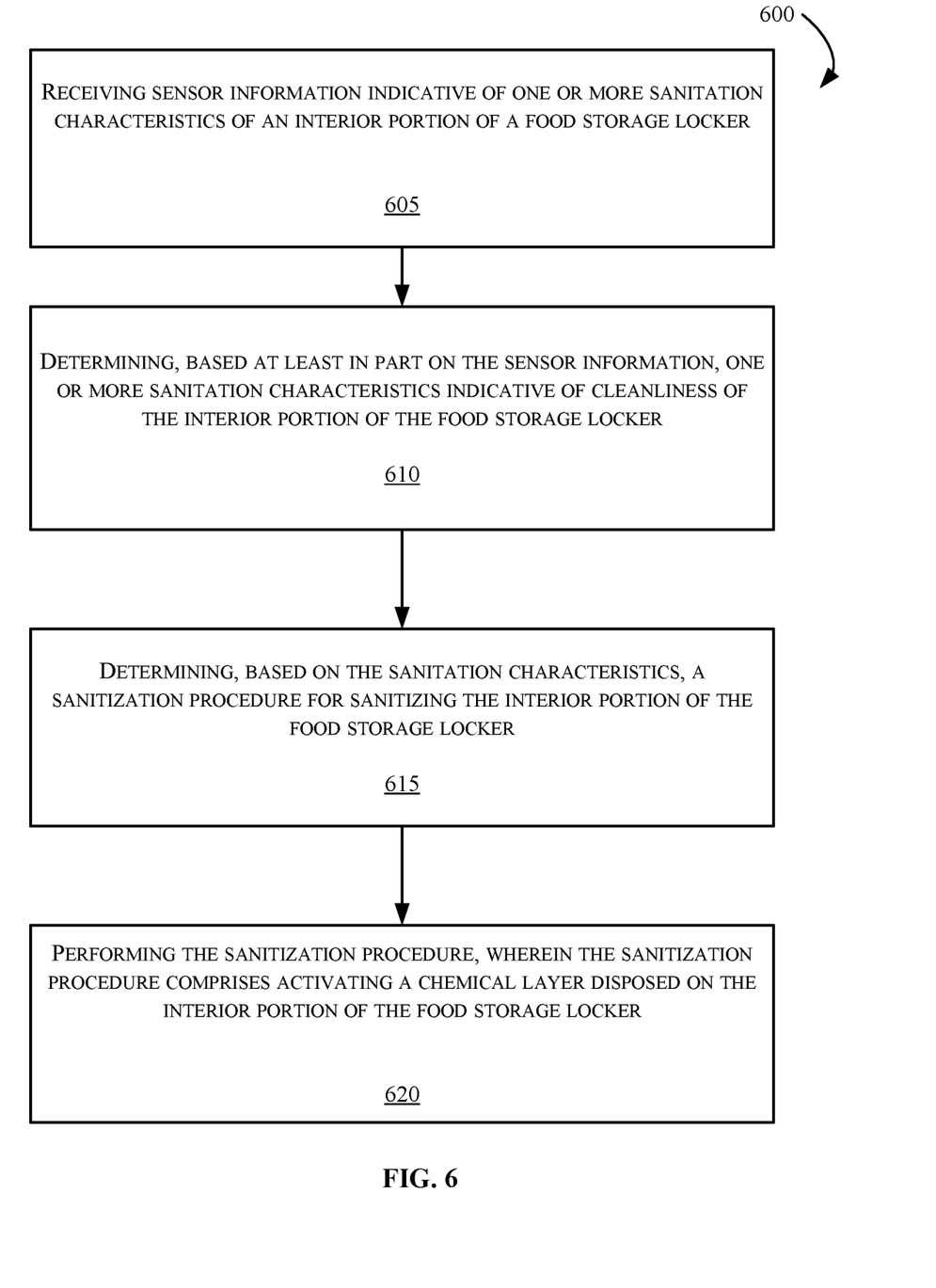
FIG. 6 is a flow diagram depicting example steps for performing a method in accordance with the present disclosure.

FIG. 6 is a flowchart of an example method 600 of the present disclosure. The method generally includes a step 605 of receiving sensor information indicative of one or more sanitation characteristics of an interior portion of a food storage locker. This step can further include determining, based at least in part on the sensor information, an identity associated with a food provider, and saving, to a computer-readable memory, information indicative of the identity of the food storage provider.

Next, the method can include a step 610 of determining, based at least in part on the sensor information, one or more sanitation characteristics indicative of cleanliness of the interior portion of the food storage locker, and performing a sanitization procedure for sanitizing the interior portion of the food storage locker. This step can be done, at least in part, by matching, based at least in part on the sensor information, a sanitization characteristic of the one or more predetermined sanitation characteristics in a characteristics database.

Next, the method includes a step 615 of determining, based on the sanitation characteristics, a sanitization procedure for sanitizing the interior portion of the food storage locker. The sanitization procedure can include a photonic stimulus type, a wavelength value, a control time for generating photonic output, a message that may be sent to one or more other devices indicative of tasks to be performed, and other information.

Next, the method includes a step 620 of performing the sanitization procedure, wherein the sanitization procedure comprises activating a chemical layer disposed on the interior portion of the food storage locker. This process can be performed using a photonic output array by activating, with one or more processor(s), the photonic output array directed towards an interior surface of the food storage locker. In some aspects, the method includes energizing a long-persistence phosphor portion of the chemical layer via a UV photonic output associated with the photonic output array, where energizing the long-persistence phosphor portion of the chemical layer comprises providing a photonic stimulus having a wavelength within a predetermined range of wavelength values. In other aspects, energizing the long-persistence phosphor portion of the chemical layer further comprises providing the photonic stimulus for a predetermined time period.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a feature, structure, or characteristic is described in connection with an embodiment, one skilled in the art will recognize such feature, structure, or characteristic in connection with other embodiments whether or not explicitly described.

It should also be understood that the word "example" as used herein is intended to be non-exclusionary and non-limiting in nature. More particularly, the word "exemplary" as used herein indicates one among several examples, and it should be understood that no undue emphasis or preference is being directed to the particular example being described.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Computing devices may include computer-executable instructions, where the instructions may be executable by one or more computing devices such as those listed above and stored on a computer-readable medium.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating various embodiments and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation. All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A computer-implemented method, comprising:
   receiving sensor information indicative of one or more sanitation characteristics of an interior portion of a food storage locker;
   determining, based at least in part on the sensor information, one or more sanitation characteristics indicative of cleanliness of the interior portion of the food storage locker;
   matching, based at least in part on the sensor information, a sanitization characteristic of the one or more sanitation characteristics to data stored in a characteristics database associated with a type of contamination;
   determining, based on the type of contamination, a sanitization procedure for sanitizing the interior portion of the food storage locker; and
   performing the sanitization procedure, wherein the sanitization procedure comprises activating a chemical layer disposed on the interior portion of the food storage locker,
   wherein receiving the sensor information indicative of one or more sanitation characteristics of the interior portion of the food storage locker further comprises:
      determining, based at least in part on the sensor information, an identity associated with a food provider, wherein the sensor information comprises a video feed of at least one individual accessing the food storage locker; and
      saving, to a computer-readable memory, information indicative of the identity.

2. The computer-implemented method according to claim 1, wherein performing the sanitization procedure comprises:
   activating a photonic output array directed towards an interior surface of the food storage locker based at least in part on pattern matching techniques and the data stored in the characteristics database.

3. The computer-implemented method according to claim 2, further comprising energizing a long-persistence phosphor portion of the chemical layer via an ultraviolet (UV) photonic output associated with the photonic output array.

4. The computer-implemented method according to claim 3, wherein energizing the long-persistence phosphor portion of the chemical layer comprises providing a photonic stimulus having a wavelength within a predetermined range of wavelength values.

5. The computer-implemented method according to claim 4, wherein energizing the long-persistence phosphor portion of the chemical layer further comprises providing the photonic stimulus for a predetermined time period.

6. The computer-implemented method according to claim 1, wherein receiving the sensor information indicative of one or more sanitation characteristics of the interior portion of the food storage locker further comprises:
   receiving one or more of a temperature associated with the interior portion of the food storage locker, a temperature associated with an exterior portion of the food storage locker, and time information associated with a door latch operation of the food storage locker.

7. The computer-implemented method according to claim 1, wherein performing the sanitization procedure further comprises:
   generating an encrypted message associated with the food storage locker, the encrypted message indicative of a sanitation event that indicates service readiness of the food storage locker; and
   transmitting, via a wireless communications network, the encrypted message from the food storage locker to a mobile device associated with a consumer.

* * * * *